US011172953B2

(12) United States Patent
Norton et al.

(10) Patent No.: US 11,172,953 B2
(45) Date of Patent: Nov. 16, 2021

(54) ARTHROSCOPIC DEVICES AND METHODS

(71) Applicant: RELIGN Corporation, Campbell, CA (US)

(72) Inventors: Jeffrey Norton, Emerald Hills, CA (US); Evan Nessim, Los Gatos, CA (US); Aaron Germain, San Jose, CA (US)

(73) Assignee: Relign Corporation, Campbell, CA (US)

( * ) Notice: Subject to any disclaimer, the term of this patent is extended or adjusted under 35 U.S.C. 154(b) by 416 days.

(21) Appl. No.: 16/129,620

(22) Filed: Sep. 12, 2018

(65) Prior Publication Data

US 2019/0008541 A1    Jan. 10, 2019

Related U.S. Application Data

(63) Continuation-in-part of application No. 15/483,940, filed on Apr. 10, 2017, now Pat. No. 10,595,889.
(Continued)

(51) Int. Cl.
*A61B 18/12* (2006.01)
*A61B 17/32* (2006.01)
(Continued)

(52) U.S. Cl.
CPC .. *A61B 17/320016* (2013.01); *A61B 17/1608* (2013.01); *A61B 17/1626* (2013.01);
(Continued)

(58) Field of Classification Search
CPC ............ A61B 17/1608; A61B 17/1624; A61B 17/32202; A61B 2017/320024–320032;
(Continued)

(56) References Cited

U.S. PATENT DOCUMENTS 2,513,564 A    7/1950  Ingwersen
2,514,545 A    7/1950  Ingwersen
(Continued)

FOREIGN PATENT DOCUMENTS

CN    200998857 Y    1/2008
CN    111629675 A    9/2020
(Continued)

OTHER PUBLICATIONS

"U.S. Appl. No. 15/483,940, filed Sep. 25, 2019 to Non Final Office Action dated Aug. 20, 2019", 13 pgs.
(Continued)

*Primary Examiner* — Daniel W Fowler
(74) *Attorney, Agent, or Firm* — Schwegman Lundberg & Woessner, P.A.

(57) ABSTRACT

An arthroscopic device is used with a hand piece having a motor drive with a rotating drive shaft. An elongate probe extending along a longitudinal axis and includes a proximal hub on a proximal end. The proximal hub detachably couples to the hand piece, and an openable-closeable jaw structure is disposed on a distal end of the elongate probe. A conversion mechanism carried by the hub converts a rotational motion of the motor drive shaft to a longitudinal motion of an actuator member. The actuator member drives the jaw structure between jaw-open and jaw-closed positions to resect bone and other hard tissues.

28 Claims, 12 Drawing Sheets

Related U.S. Application Data

(60) Provisional application No. 62/563,234, filed on Sep. 26, 2017, provisional application No. 62/321,114, filed on Apr. 11, 2016, provisional application No. 62/325,326, filed on Apr. 20, 2016.

(51) Int. Cl.
*A61B 17/16* (2006.01)
*A61B 18/14* (2006.01)
*A61B 18/00* (2006.01)
*A61B 17/00* (2006.01)

(52) U.S. Cl.
CPC .... *A61B 17/32002* (2013.01); *A61B 18/1445* (2013.01); *A61B 17/1624* (2013.01); *A61B 17/1628* (2013.01); *A61B 2017/0046* (2013.01); *A61B 2017/00137* (2013.01); *A61B 2017/00398* (2013.01); *A61B 2017/320028* (2013.01); *A61B 2018/00565* (2013.01); *A61B 2018/00601* (2013.01); *A61B 2018/1457* (2013.01); *A61B 2217/005* (2013.01)

(58) Field of Classification Search
CPC ............ A61B 18/1442; A61B 18/1445; A61B 2018/145; A61B 2018/1452
See application file for complete search history.

(56) References Cited

U.S. PATENT DOCUMENTS

| | | |
|---|---|---|
| 2,625,625 A | 1/1953 | Ingwersen |
| 2,689,895 A | 9/1954 | Ingwersen |
| 3,611,023 A | 10/1971 | Souza, Jr. et al. |
| 3,838,242 A | 9/1974 | Goucher |
| 3,848,211 A | 11/1974 | Russell |
| 3,868,614 A | 2/1975 | Riendeau |
| 3,899,829 A | 8/1975 | Storm et al. |
| 3,903,891 A | 9/1975 | Brayshaw |
| 3,945,375 A | 3/1976 | Banko |
| 4,060,088 A | 11/1977 | Morrison, Jr. et al. |
| 4,272,687 A | 6/1981 | Borkan |
| 4,522,206 A * | 6/1985 | Whipple ............ A61B 17/1608 600/565 |
| 4,781,175 A | 11/1988 | McGreevy et al. |
| 4,815,462 A | 3/1989 | Clark |
| 4,895,146 A | 1/1990 | Draenert |
| 4,936,842 A | 6/1990 | D'Amelio et al. |
| 4,977,346 A | 12/1990 | Gibson et al. |
| 5,012,495 A | 4/1991 | Munroe et al. |
| 5,122,138 A | 6/1992 | Manwaring |
| 5,207,675 A | 5/1993 | Canady |
| 5,256,138 A | 10/1993 | Burek et al. |
| 5,281,217 A | 1/1994 | Edwards et al. |
| 5,433,721 A | 7/1995 | Hooven et al. |
| 5,449,356 A | 9/1995 | Walbrink et al. |
| 5,490,854 A | 2/1996 | Fisher et al. |
| 5,490,860 A | 2/1996 | Middle et al. |
| 5,520,634 A | 5/1996 | Fox et al. |
| 5,620,415 A * | 4/1997 | Lucey ................ A61B 17/1608 604/22 |
| 5,641,251 A | 6/1997 | Leins et al. |
| 5,669,907 A | 9/1997 | Platt, Jr. et al. |
| 5,683,366 A | 11/1997 | Eggers et al. |
| 5,702,420 A | 12/1997 | Sterling et al. |
| 5,720,745 A | 2/1998 | Farin et al. |
| 5,759,185 A | 6/1998 | Grinberg |
| 5,766,195 A | 6/1998 | Nobles |
| 5,776,092 A | 7/1998 | Farin et al. |
| 5,810,809 A | 9/1998 | Rydell |
| 5,823,971 A | 10/1998 | Robinson et al. |
| 5,839,897 A | 11/1998 | Bordes |
| 5,849,010 A | 12/1998 | Wurzer et al. |
| 5,857,995 A | 1/1999 | Thomas et al. |
| 5,873,855 A | 2/1999 | Eggers et al. |
| 5,888,198 A | 3/1999 | Eggers et al. |
| 5,891,095 A | 4/1999 | Eggers et al. |
| 5,904,681 A | 5/1999 | West, Jr. |
| 5,913,867 A | 6/1999 | Dion |
| 5,925,055 A | 7/1999 | Adrian et al. |
| 5,954,731 A | 9/1999 | Yoon |
| 5,957,884 A | 9/1999 | Hooven |
| 5,964,752 A | 10/1999 | Stone |
| 5,989,248 A | 11/1999 | Tu et al. |
| 6,007,553 A | 12/1999 | Hellenkamp et al. |
| 6,013,075 A | 1/2000 | Avramenko et al. |
| 6,013,076 A | 1/2000 | Goble et al. |
| 6,024,733 A | 2/2000 | Eggers et al. |
| 6,032,674 A | 3/2000 | Eggers et al. |
| 6,039,736 A | 3/2000 | Platt, Jr. |
| 6,056,747 A | 5/2000 | Saadat et al. |
| 6,066,134 A | 5/2000 | Eggers et al. |
| 6,099,523 A | 8/2000 | Kim et al. |
| 6,142,992 A | 11/2000 | Cheng et al. |
| 6,149,620 A | 11/2000 | Baker et al. |
| 6,159,208 A | 12/2000 | Hovda et al. |
| 6,193,715 B1 | 2/2001 | Wrublewski et al. |
| 6,225,883 B1 | 5/2001 | Wellner et al. |
| 6,235,020 B1 | 5/2001 | Cheng et al. |
| 6,238,391 B1 | 5/2001 | Olsen et al. |
| 6,261,241 B1 | 7/2001 | Burbank et al. |
| 6,296,636 B1 | 10/2001 | Cheng et al. |
| 6,332,886 B1 | 12/2001 | Green et al. |
| 6,348,051 B1 | 2/2002 | Farin et al. |
| 6,394,956 B1 | 5/2002 | Chandrasekaran et al. |
| 6,413,256 B1 | 7/2002 | Truckai et al. |
| 6,419,674 B1 | 7/2002 | Bowser et al. |
| 6,443,948 B1 | 9/2002 | Suslov |
| 6,475,215 B1 | 11/2002 | Tanrisever |
| 6,538,549 B1 | 3/2003 | Renne et al. |
| 6,579,289 B2 | 6/2003 | Schnitzler |
| 6,610,059 B1 | 8/2003 | West, Jr. |
| 6,629,986 B1 | 10/2003 | Ross et al. |
| 6,632,220 B1 | 10/2003 | Eggers et al. |
| 6,656,195 B2 | 12/2003 | Peters et al. |
| 6,669,694 B2 | 12/2003 | Shadduck |
| 6,720,856 B1 | 4/2004 | Pellon et al. |
| 6,780,178 B2 | 8/2004 | Palanker et al. |
| 6,783,533 B2 | 8/2004 | Green et al. |
| 6,821,275 B2 | 11/2004 | Truckai et al. |
| 6,827,725 B2 | 12/2004 | Batchelor et al. |
| 6,837,884 B2 | 1/2005 | Woloszko |
| 6,837,888 B2 | 1/2005 | Ciarrocca et al. |
| 6,890,332 B2 | 5/2005 | Truckai et al. |
| 6,902,564 B2 | 6/2005 | Morgan et al. |
| 6,979,332 B2 | 12/2005 | Adams |
| 7,087,054 B2 | 8/2006 | Truckai et al. |
| 7,112,200 B2 | 9/2006 | Cucin |
| 7,150,747 B1 | 12/2006 | McDonald et al. |
| 7,220,261 B2 | 5/2007 | Truckai et al. |
| 7,309,849 B2 | 12/2007 | Truckai et al. |
| 7,549,989 B2 | 6/2009 | Morgan et al. |
| 7,674,263 B2 | 3/2010 | Ryan et al. |
| 7,678,069 B1 | 3/2010 | Baker et al. |
| 7,713,269 B2 | 5/2010 | Auge, II et al. |
| 7,717,710 B2 | 5/2010 | Danger et al. |
| 7,744,595 B2 | 6/2010 | Truckai et al. |
| 7,771,422 B2 | 8/2010 | Auge et al. |
| 7,819,861 B2 | 10/2010 | Auge et al. |
| 7,819,864 B2 | 10/2010 | Morgan et al. |
| 7,955,331 B2 | 6/2011 | Truckai et al. |
| 8,012,153 B2 | 9/2011 | Woloszko et al. |
| 8,016,823 B2 | 9/2011 | Shadduck |
| 8,062,319 B2 | 11/2011 | O'Quinn et al. |
| 8,075,555 B2 | 12/2011 | Truckai et al. |
| 8,192,424 B2 | 6/2012 | Woloszko |
| 8,192,428 B2 | 6/2012 | Truckai et al. |
| 8,197,483 B2 | 6/2012 | Faulhaber et al. |
| 8,221,404 B2 | 7/2012 | Truckai et al. |
| 8,323,280 B2 | 12/2012 | Germain et al. |
| 8,333,763 B2 | 12/2012 | Truckai et al. |
| 9,005,203 B2 | 4/2015 | Nelson et al. |
| 9,179,923 B2 | 11/2015 | Gubellini et al. |
| 9,504,521 B2 | 11/2016 | Deutmeyer et al. |

(56) References Cited

U.S. PATENT DOCUMENTS

| | | |
|---|---|---|
| 9,585,675 B1 | 3/2017 | Germain et al. |
| 9,603,656 B1 | 3/2017 | Germain et al. |
| 9,681,913 B2 | 6/2017 | Orczy-Timko et al. |
| 10,004,556 B2 | 6/2018 | Orczy-Timko et al. |
| 10,595,889 B2 | 3/2020 | Germain et al. |
| 2003/0014051 A1 | 1/2003 | Woloszko |
| 2003/0083681 A1 | 5/2003 | Moutafis et al. |
| 2003/0125727 A1 | 7/2003 | Truckai et al. |
| 2003/0163135 A1 | 8/2003 | Hathaway |
| 2004/0044341 A1 | 3/2004 | Truckai et al. |
| 2004/0167427 A1 | 8/2004 | Quick et al. |
| 2005/0015085 A1 | 1/2005 | McClurken et al. |
| 2005/0075630 A1 | 4/2005 | Truckai et al. |
| 2005/0228372 A1 | 10/2005 | Truckai et al. |
| 2006/0058782 A1 | 3/2006 | Truckai et al. |
| 2006/0074345 A1 | 4/2006 | Hibner |
| 2006/0178670 A1 | 8/2006 | Woloszko et al. |
| 2006/0224154 A1 | 10/2006 | Shadduck et al. |
| 2007/0213704 A1 | 9/2007 | Truckai et al. |
| 2008/0003255 A1 | 1/2008 | Kerr et al. |
| 2008/0027448 A1 | 1/2008 | Raus et al. |
| 2008/0103494 A1 | 5/2008 | Rioux et al. |
| 2008/0188848 A1 | 8/2008 | Deutmeyer et al. |
| 2008/0208249 A1 | 8/2008 | Blain et al. |
| 2008/0249533 A1 | 10/2008 | Godin |
| 2008/0249553 A1 | 10/2008 | Gruber et al. |
| 2009/0076498 A1 | 3/2009 | Saadat et al. |
| 2009/0082766 A1* | 3/2009 | Unger ............... A61B 18/1445 606/51 |
| 2009/0131932 A1* | 5/2009 | Vakharia ................ A61L 2/08 606/48 |
| 2009/0209946 A1 | 8/2009 | Swayze et al. |
| 2009/0270849 A1 | 10/2009 | Truckai et al. |
| 2010/0057078 A1 | 3/2010 | Arts et al. |
| 2010/0087816 A1 | 4/2010 | Roy |
| 2010/0100091 A1 | 4/2010 | Truckai |
| 2010/0305565 A1 | 12/2010 | Truckai et al. |
| 2011/0160723 A1 | 6/2011 | Tullis et al. |
| 2011/0282373 A1 | 11/2011 | Chekan et al. |
| 2012/0172889 A1* | 7/2012 | Chin ............... A61B 17/32002 606/119 |
| 2012/0209112 A2 | 8/2012 | Patel et al. |
| 2012/0245580 A1 | 9/2012 | Germain et al. |
| 2012/0310256 A1 | 12/2012 | Brisson |
| 2012/0330292 A1 | 12/2012 | Shadduck et al. |
| 2013/0041360 A1 | 2/2013 | Farritor et al. |
| 2013/0122461 A1 | 5/2013 | Shioiri |
| 2013/0172870 A1 | 7/2013 | Germain et al. |
| 2013/0253498 A1 | 9/2013 | Germain et al. |
| 2013/0267937 A1 | 10/2013 | Shadduck et al. |
| 2013/0296847 A1 | 11/2013 | Germain et al. |
| 2013/0296849 A1 | 11/2013 | Germain et al. |
| 2013/0317492 A1 | 11/2013 | Truckai et al. |
| 2013/0317493 A1 | 11/2013 | Truckai et al. |
| 2013/0331833 A1 | 12/2013 | Bloom |
| 2014/0005680 A1 | 1/2014 | Shelton, IV et al. |
| 2014/0012238 A1 | 1/2014 | Chen et al. |
| 2014/0025046 A1 | 1/2014 | Williams et al. |
| 2014/0100567 A1 | 4/2014 | Edwards et al. |
| 2014/0114300 A1 | 4/2014 | Orczy-Timko et al. |
| 2014/0336643 A1 | 11/2014 | Orczy-timko et al. |
| 2015/0209061 A1 | 7/2015 | Johnson et al. |
| 2015/0272569 A1 | 10/2015 | Leimbach et al. |
| 2016/0081737 A1 | 3/2016 | Germain et al. |
| 2016/0113706 A1 | 4/2016 | Truckai et al. |
| 2016/0157916 A1 | 6/2016 | Germain et al. |
| 2017/0027599 A1 | 2/2017 | Bek et al. |
| 2017/0128083 A1 | 5/2017 | Germain et al. |
| 2017/0172648 A1 | 6/2017 | Germain et al. |
| 2017/0224368 A1 | 8/2017 | Germain et al. |
| 2017/0252099 A1 | 9/2017 | Orczy-Timko et al. |
| 2017/0258512 A1 | 9/2017 | Germain et al. |
| 2017/0258519 A1 | 9/2017 | Germain et al. |
| 2017/0290602 A1 | 10/2017 | Germain et al. |
| 2019/0008537 A1 | 1/2019 | Kirstgen et al. |
| 2020/0178997 A1 | 6/2020 | Germain et al. |

FOREIGN PATENT DOCUMENTS

| | | |
|---|---|---|
| DE | 102005059864 A1 | 6/2007 |
| EP | 0119405 A1 | 9/1984 |
| EP | 1034747 A1 | 9/2000 |
| EP | 2397084 A2 | 12/2011 |
| EP | 3442446 A1 | 2/2019 |
| EP | 3687426 A1 | 8/2020 |
| WO | WO-0053112 A2 | 9/2000 |
| WO | WO-0062685 A1 | 10/2000 |
| WO | WO-0053112 A3 | 12/2000 |
| WO | WO-2007073867 A1 | 7/2007 |
| WO | WO-2014165715 A1 | 10/2014 |
| WO | WO-2015100310 A1 | 7/2015 |
| WO | WO-2017151993 A1 | 9/2017 |
| WO | WO-2017156335 A1 | 9/2017 |
| WO | WO-2017156343 A1 | 9/2017 |
| WO | WO-2017180654 A1 | 10/2017 |
| WO | WO-2019067460 A1 | 4/2019 |

OTHER PUBLICATIONS

"International Application Serial No. PCT/US2017/027053, International Preliminary Report on Patentability dated Oct. 25, 2018", 10 pgs.

"International Application Serial No. PCT/US2018/052696, International Preliminary Report on Patentability dated Apr. 9, 2020", 6 pgs.

Co-pending U.S. Appl. No. 16/789,845, filed Feb. 13, 2020.

European search report and opinion dated Feb. 3, 2020 for EP Application No. 17783001.5.

European search report and opinion dated Oct. 2, 2019 for EP Application No. 17764155.2.

European search report dated Nov. 2, 2009 for EP Application No. 01967968.7.

International search report and opinion dated Jul. 15, 2016 for PCT/US2016/027157.

International Search Report and Written Opinion dated Mar. 8, 2017 for International PCT Patent Application No. PCT/US2016/058179.

International Search Report and Written Opinion dated May 16, 2017 for International PCT Patent Application No. PCT/US2017/016002.

International Search Report and Written Opinion dated May 22, 2017 for International PCT Patent Application No. PCT/US2017/021675.

International Search Report and Written Opinion dated May 23, 2012 for International PCT Patent Application No. PCT/US2012/023390.

International Search Report and Written Opinion dated Aug. 1, 2017 for International PCT Patent Application PCT/US2017/021687.

International Search Report and Written Opinion dated Aug. 22, 2017 for International PCT Patent Application No. PCT/US2017/027053.

International Search Report and Written Opinion dated Nov. 29, 2016 for International Application No. PCT/US2016/058145.

International search report dated Jan. 14, 2002 for PCT/US2001/025409.

International search report with written opinion dated Jan. 24, 2019 for PCT/US2018/052696.

Kim, et al. Optical feedback signal for ultra short pulse ablation of tissue. Appl. Surface Sci. 1998; 127-129:857-862.

Notice of Allowance dated Jan. 6, 2017 for U.S. Appl. No. 14/960,084.

Notice of Allowance dated Feb. 8, 2017 for U.S. Appl. No. 14/977,256.

Notice of Allowance dated Feb. 16, 2017 for U.S. Appl. No. 15/096,546.

Notice of Allowance dated Nov. 13, 2019 for U.S. Appl. No. 15/483,940.

Notice of Allowance dated Dec. 2, 2016 for U.S. Appl. No. 14/977,256.

(56) References Cited

OTHER PUBLICATIONS

Notice of Allowance dated Dec. 30, 2016 for U.S. Appl. No. 14/977,256.
Office action dated May 3, 2016 for U.S. Appl. No. 14/960,084.
Office action dated Jul. 28, 2016 for U.S. Appl. No. 14/977,256.
Office Action dated Aug. 18, 2016 for U.S. Appl. No. 14/960,084.
Office action dated Aug. 20, 2019 for U.S. Appl. No. 15/483,940.
Office Action dated Sep. 26, 2016 for U.S. Appl. No. 15/096,546.
Partial supplementary European search report and provisional opinion dated Oct. 31, 2019 for EP Application No. 17783001.5.
Pedowitz, et al. Arthroscopic surgical tools: a source of metal particles and possible joint damage. Arthroscopy. Sep. 2013;29(9):1559-65. doi: 10.1016/j.arthro.2013.05.030. Epub Jul. 30, 2013.
Smith & Nephew. Dyonics Bonecutter Electroblade. Webpage. Accessed Feb. 28, 2017. 1 page. URL: https://www.smith-nephew.com/professional/products/all-products/dyonics-bonecutter-electroblade/.
Tucker et al. Histologic characteristics of electrosurgical injuries. J. Am. Assoc. Gyneco. Laproscopy. 1997; 4(2):857-862.
Volpato, et al. Application of Zirconia in Dentistry: Biological, Mechanical and Optical Considerations. Advances in ceramics—Electric and Magnetic Ceramics, Bioceramics, Ceramics and Environment. Sep. 6, 2011. pp. 397-420. DOI: 10.5772/21630.
U.S. Appl. No. 15/483,940, U.S. Pat. No. 10,595,889, filed Apr. 10, 2017, Arthroscopic Devices and Methods.
U.S. Appl. No. 16/789,845, filed Feb. 13, 2020, Arthroscopic Devices and Methods.
"European Application Serial No. 17783001.5, Intention to Grant dated Mar. 29, 2021", 28 pgs.
"European Application Serial No. 17783001.5, Response filed Aug. 21, 2020 to Extended European Search Report dated Feb. 3, 2020", 31 pgs.
"European Application Serial No. 18860916.8, Extended European Search Report dated May 19, 2021", 9 pgs.

\* cited by examiner

ARTHROSCOPIC DEVICES AND METHODS

CROSS-REFERENCE TO RELATED APPLICATIONS

This application claims the benefit of provisional application No. 62/563,234, filed on Sep. 26, 2017, the full disclosure of which is incorporated herein by reference.

This application is also a continuation-in-part of application Ser. No. 15/483,940, filed on Apr. 10, 2017, which claimed the benefit of provisional application Nos. 62/321,114, filed on Apr. 11, 2017, and 62/325,326, filed on Apr. 20, 2017, the full disclosures of which are incorporated herein by reference.

BACKGROUND OF THE INVENTION

1. Field of the Invention

This invention relates to arthroscopic tissue cutting and removal devices by which anatomical tissues may be cut and removed from a joint or other site. More specifically, this invention relates to instruments with a motor driven openable-closeable jaw that cuts tissue.

2. Description of the Background Art

In several surgical procedures including a meniscectomy, anterior cruciate ligament reconstruction involving notchplasty, and arthroscopic resection of the acromioclavicular joint, there is a need for cutting and removal of bone and soft tissue. Currently, surgeons use arthroscopic shavers and burrs having rotational cutting surfaces to remove hard tissue in such procedures.

Parent application Ser. No. 15/483,940 describes a particular arthroscopic cutter including a hand piece having a motor drive. A shaft assembly includes an openable-closable jaw structure at a working end and a hub at the other end of the shaft. The hub is configured for detachable coupling to the hand piece, and the motor drive is configured to axially reciprocate an actuator member to drive the jaw structure when the hub is coupled to the hand piece. The motor drive has a rotating shaft, and the rotation is converted to axial reciprocation by an epicyclic gear mechanism where a tilted cam surface is reciprocated by a stud that travels in a circular pattern to engage the cam surface. While this design is efficient and provides for rapid actuation of the jaw structure, the closing force transmitted to the jaw structure can be limited. Such limited force can be a drawback when resecting bone and other hard tissue.

For these reasons, it would be desirable to provide improved arthroscopic and other surgical cutters having reciprocating actuator elements that are able to transmit large closing forces to jaw structures and other mechanical end effectors in order to more effectively remove bone and other hard tissues. It would be further desirable if such improved surgical cutters were able to also remove soft tissue rapidly. At least some of these objectives will be met by the inventions described and claimed below.

SUMMARY OF THE INVENTION

In a first aspect, the present invention provides an arthroscopic device which can be used with a hand piece for performing laparoscopic and other surgical procedures. The hand piece will have a motor drive with a rotating shaft, and the arthroscopic device is typically detachably or removably connectable to the hand piece so that the device may be disposable and the hand piece may be reusable. The device comprises an elongate probe extending along a longitudinal axis. A proximal hub on a proximal end of the elongate probe is configured for detachable coupling to the hand piece, and an openable-closable jaw structure is disposed on a distal end of the elongate probe. A conversion mechanism is carried by the hub and is configured to convert a rotational motion provided by a drive shaft of the motor drive to a longitudinal motion of an actuator member. The actuator member is further configured for driving the jaw structure between jaw-open and jaw-closed positions.

In particular embodiments, the conversion mechanisms of the arthroscopic devices of the present invention may include at least a first drive element having external helical threads configured to engage inner helical threads formed in the hub, typically over an inner surface in a proximal cavity of the hub. The helical threads on the first drive element will have a pitch and spacing which matches those of the inner helical threads formed in the hub cavity so that rotation of the first drive element will axially translate the first drive element relative to the hub. The direction of axial translation will depend on the direction of rotation of the motor drive shaft, and the pitch and spacing of the helical threads will be chosen to provide a desired ratio of rotations per millimeter of translation as discussed in more detail below.

The conversion mechanism will typically further comprise at least a second drive element having external helical threads that engage internal helical threads formed in the first drive element. The outer helical threads on the second drive element will have a pitch and spacing which matches those of the internal helical threads formed in the first drive element so that rotation of the first drive element will simultaneous axially translate the second drive element relative to the first drive element relative in addition to translating the first drive element realtive to the hub.

In particular, the pitch and spacing of the helical threads mating between the first and second drive elements will be selected to axially translate the second drive in a direction opposite to the direction in which the first drive element is being driven. By having the first and second drive elements move in opposite directions relative to the hub, the number of rotations of the drive shaft required to translate the second drive element over a fixed distance can be maximized thus maximizing the mechanical advantage obtained in driving the jaw structure. The pitches of the inner helical threads and the outer helical threads on the first drive element must, of course, differ so that there is a net differential in the travel of the second drive element relative to the hub so that the actuator member can be advanced and retracted. In specific embodiments, the second drive element is nested within a central cavity of the first drive element so that the external threads on the second drive element concentrically engage the internal threads disposed on an inner wall of the central cavity of the first drive element.

In further specific embodiments, the arthroscopic devices may further comprise a rotatable drive coupling configured to be engaged and driven by the rotating shaft of the motor drive as well as to couple to and rotate the first drive element. Usually, the rotatable drive coupling is inhibited from axial translation relative to the hub while the first drive element is free to both rotate and axially translate relative to the hub. The second drive element coming, in contrast, is inhibited from rotation but is free to axially translate relative to the hub. In this way, rotation of the motor drive shaft in a first direction will cause the first drive element to axially translate in a distal direction within the cavity of the hub while simultaneously causing the second drive element to proximally translate relative to the hub. The rate at which the first drive element distally translates may be greater or less than that at which the second drive element proximally translates so that there is a net advancement or retraction of the second drive element which is connected to the jaw structure. Such an arrangement is advantageous since it increases the total number of rotations applied by the motor drive unit to move the second drive element (and thus drive the moveable jaws) over a given distance. This greater number of rotations come in turn, provides a mechanical advantage which increases the force being applied to the movable jaws relative to the torque being applied by the drive motor. Such increased force is further advantageous when hard tissues, such as bone, are to be resected.

In further specific embodiments, the actuator member is coupled to a pivot mechanism for opening and closing the jaw structure. The pivot mechanism may be further configured to provide a lever element to increase the closing force being applied to the jaw structure. In other specific aspects, longitudinal portions of the inner and outer threads of the first drive element may overlap one another, reducing the length and volume required to accommodate the conversion mechanism. The inner and outer threads of the first drive element will have different thread pitches, where the particular ratios of the pitches will be selected to control the advancement and "gear ratio" of the conversion mechanism. In this way, the different thread pitches may be chosen to amplify torque in moving the jaw structure from the jaw-open position toward the jaw-closed position.

In exemplary embodiments, the conversion mechanism is configured to move the actuator member longitudinally in a stroke ranging from 0.5 mm to 5 mm to actuate the draw structure from a jaw-open position to a jaw-closed position. And still further specific embodiments, for the conversion mechanism will be configured to convert from 1 to 20 rotations of the drive coupling to provide the stroke of the jaw mechanism. Preferably, the conversion mechanism may be configured to convert from 2 to 10 rotations of the drive coupling to provide the stroke.

Optionally, the arthroscopic devices of the present invention may further comprise a controller for controlling the motor shaft, where then the controller may actuate the motor shaft to rotate the motor shaft in a first rotational direction to the jaws of the jaw structure apart toward the jaw-open position and to rotate the motor shaft in an opposite rotational direction to move the jaw structure toward the jaw-closed position. The controller may be configured to open and close the jaw structure in single strokes or alternatively to open and close the jaws at a rate ranging typically from one closure per second to 20 closures per second. The controller may further be configured to move the jaw structure to a jaw-open or jaw-closed default position when the motor drive is deactivated.

In a second aspect of the present invention, an arthroscopic device comprises a hand piece having a motor drive with a rotating shaft. An elongate probe extends along the longitudinal access for a proximal hub to a distal openable-closable draw structure. The hub is configured for detachable coupling to the hand piece, and a drive coupling is disposed on the hub for engaging the motor shaft. A screw mechanism in hub converts rotational motion of the drive coupling to longitudinal motion of an actuator member which is configured for actuating the jaw structure between jaw-open and jaw-closed position. A controller is provided to operate the motor in order to move the jaw structure from the jaw-open position to the jaw-closed position and back to the jaw-open position at a rate ranging from one time per second to 20 times per second.

In a third aspect of the present invention, a method for resecting tissue comprises providing a hand piece with a motor drive and a probe, where the probe has a proximal hub and a distal jaw structure. A rotational glide shaft of the motor drive is coupled to the proximal hub on the probe and the hand piece. The distal jaw structure is engaged against target tissue and a rotational torque from the motor drive is supplied to a conversion mechanism in the proximal hub. The conversion mechanism axially translates an actuator member to drive the jaw structure between the jaw-open and jaw-closed positions. The conversion mechanism is configured to convert from one to 20 rotations of the drive shaft to provide a single opening or single closing stroke of the jaw structure.

In particular embodiments of the methods, engaging may comprise advancing the distal jaw structure into a joint to engage the draw structure against bone. The motor can then be driven to open and close the jaw structure to reset the bone tissue. Usually, the motor will be actuated by a controller in any of the various control schemes described above, including single opening and closing strokes, continuous opening and closing patterns, jaw-open and jaw-closed default stopping points, and the like. On being driven contiguously, the motor drive will usually be controlled to open and close the jaws at a rate of at least one cycle per second (CPS), often from one CPS to 100 CPS.

The methods may further comprise activating a negative pressure source and communication with an interior of the probe to suction resected tissue from the jaw structure.

Specific constructions and uses of the conversion mechanism in the methods of the present invention are generally the same as those described above with respect to the apparatus of the present in mention.

In still further exemplary embodiments, the motor drive is configured to open and close the jaw structure at a rate of at least 1 CPS (cycle(s) per second), often at a rate in the range of between 1 CPS and 100 CPS, frequently at a rate in the range between 1 CPS and 10 CPS, and the like.

Other exemplary arthroscopic cutters of the present invention may include a passageway extending through the shaft assembly to the working end of the shaft. The passageway is typically configured for connection to a negative pressure source which can provide for continuous or periodic aspiration or suction of resected tissue from the operative site.

In additional exemplary embodiments, the arthroscopic cutters of the present invention may further comprise a processor configured to control the motor drive, e.g., to stop and/or start movement of a first jaw in the jaw structure relative to a second jaw of the jaw structure. Typically, the movement may be stopped in a variety of positions, such as one or more default positions. For example, a default position may be with the jaws open. In other cases, a default position may be with the jaws closed or in any other relative position between open and closed. Typically, a sensor in the hand piece will be connected to the controller and configured to sense jaw position, e.g., using a magnet coupled to the jaw structure (in one instance carried by a separate moving member coupled to the jaw structure) to indicate default and non-default positions, thus allowing motion to be stopped at a desired position.

In still further exemplary embodiments, the arthroscopic cutters of the present invention may include an actuator for actuating the motor drive to open and close the jaw structure, for example at a rate of at least 1 CPS. Such actuators may also be configured to move the jaw structure to a jaw-open position, to a jaw-closed position as well as for other purposes, such as for actuating a negative pressure source, for actuating both the motor drive and a negative pressure source, for modulating the negative pressure source in response to actuation in the motor drive, and the like. In other instances, the processor may be configured to modulate the negative pressure source relative to a fully open position, a partially open position, or a closed position of the jaw structure.

The arthroscopic cutters of the present invention, in still other embodiments, may include radio frequency (RF) electrode edge portions configured for cutting or otherwise resecting tissue. Alternative, the jaw structures may have first and second jaws including honed, or other scissor-like edge portions for shearing tissue. In still other embodiments, the jaw structure may have at least one cup-shaped jaw adapted for cutting and capturing tissue. In yet other embodiments, the jaw of the jaw structure may have a metal cutting edge, a ceramic cutting edge, or may simply comprise a ceramic material.

In a second aspect, the present invention provides methods for performing a meniscectomy. Such methods comprise providing a hand piece with a motor drive. The probe is coupled to the hand piece, where the probe has a working end with openable-closeable jaws configured to resect tissue. The motor drive is configured to open and close the jaws when the hand piece is coupled to the probe. The working end may then be advanced into a patient's joint to engage the jaws against meniscal tissue. The meniscal tissue may then be resected by actuating the motor drive to open and close the jaws.

In specific embodiments, the methods for performing meniscectomy may further comprise controlling the motor drive with a controller to actuate the jaws to resect the meniscal tissue in a single bite, or in multiple bites. For example, the motor drive may be controlled to open and close the jaws at a rate of at least 1 CPS, often at a rate of between 1 CPS and 100 CPS. At the actuating step may further comprise activating a negative pressure source in communication with an interior passageway of the probe to suction resected meniscal tissue from the working end.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

The present invention relates to tissue cutting and removal devices and related methods of use. Variations of the invention will now be described to provide an overall understanding of the principles of the form, function and methods of use of the devices disclosed herein. In general, the present invention provides an arthroscopic cutter or punch for cutting tissue that is disposable and is configured for detachable coupling to a non-disposable handle and motor drive component. This description of the general principles of this invention is not meant to limit the inventive concepts in the appended claims.

FIGS. 1-5B illustrates a tissue cutting probe 100 with a jaw structure 108 that is motor driven to close and open the jaws in a single actuation that applies high cutting forces, or alternatively, the motor drive can be actuated to close and open the jaws sequentially at 1 CPS to 100 CPS (cycle per second) to progressively nibble or cut tissue. The probe can be used in arthroscopy and other fields, for example, ENT, gynecology and urology.

Figure 1:
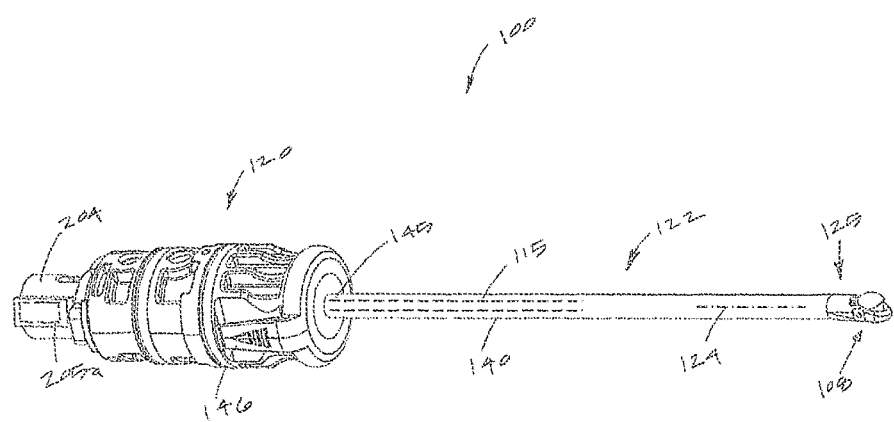
FIG. 1 is a perspective view of a disposable arthroscopic cutter or probe with a working end comprising a jaw structure having cutting edges.
Figure 2:
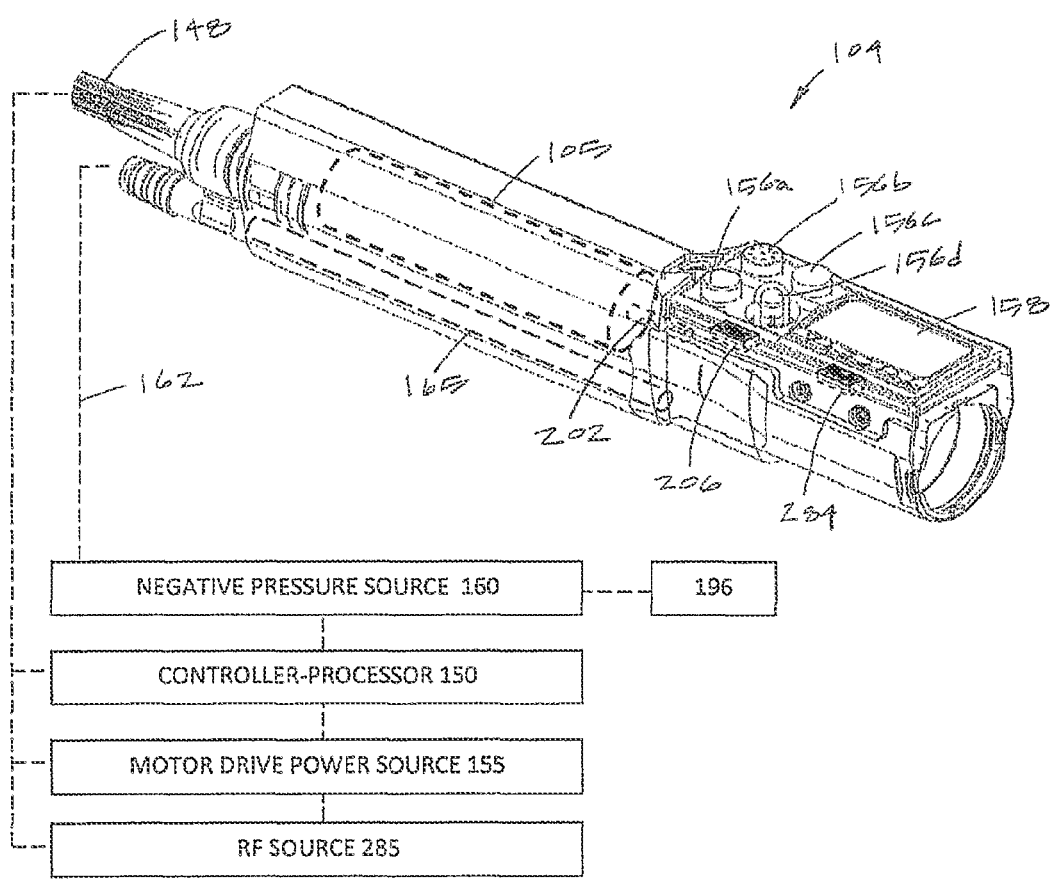
FIG. 2 is a perspective view of a hand piece with a motor drive to which the cutter of FIG. 1 can be coupled, with the handle body including an LCD screen for displaying operating parameters of device during use together with a joystick and mode control actuators on the handle.

FIG. 1 shows the disposable cutting probe 100 that is adapted for detachable coupling to a hand piece 104 and motor drive unit 105 therein as shown in FIG. 2. In the variation shown in FIGS. 1 and 3, the upper jaw 110 and lower jaw 112 are configured as cup-shaped jaws to assist in capturing and extracting tissue chips through an interior passageway 115 as will be described below (see FIGS. 5A-5B).

Referring to FIG. 1, it can be seen that cutting probe 100 has a proximal hub 120 that can be detachably coupled to the handle or hand piece 104 of FIG. 2. In the variation of FIG.

1, the probe 100 has a shaft 122 that extends about longitudinal axis 124 to a working end 125 that comprises the openable-closeable jaw structure 108 that is coupled to the motor drive 105. The shaft 122 comprises an outer sleeve 140 and an inner actuation member 142 that is adapted to reciprocate in bore 144 of the outer sleeve 140. The proximal end 145 of outer sleeve 140 is coupled in a fixed manner to the hub 120 which can be an injection molded plastic, for example, with the outer sleeve 140 insert molded therein. The outer sleeve 140 typically can be a thin wall stainless steel tube, but other materials can be used such as ceramics, metals, plastics or combinations thereof. In this variation, the reciprocation of actuation member 142 is adapted to close and open to jaw structure 108 as can be understood from FIGS. 5A-5B. Referring to FIGS. 1 and 2, the hub 120 is configured with snap-fit features 146, or other suitable features, for detachably locking the hub 120 into the hand piece 104.

In FIG. 2, it can be seen that the hand piece 104 is operatively coupled by electrical cable 148 to a controller-processor 150 which controls the motor drive unit 105. The cable 148 also couples power from electrical power source 155 to the motor drive 105. Any of the actuator buttons 156a-156d on the hand piece 104 can be used to select operating modes, such as a single open-close actuation of the jaws, or a continuous sequence of opening and closing the jaws. Further, an actuator button can be used to modulate the CPS of opening and closing the jaws. The various modes can be displayed on the LCD 158. FIG. 2 further shows that negative pressure source 160 is coupled to aspiration tubing 162 which communicates with a flow channel 165 in the hand piece 104 and passageway 115 in actuating member 142 which extends to the working end 125.

Figure 3:
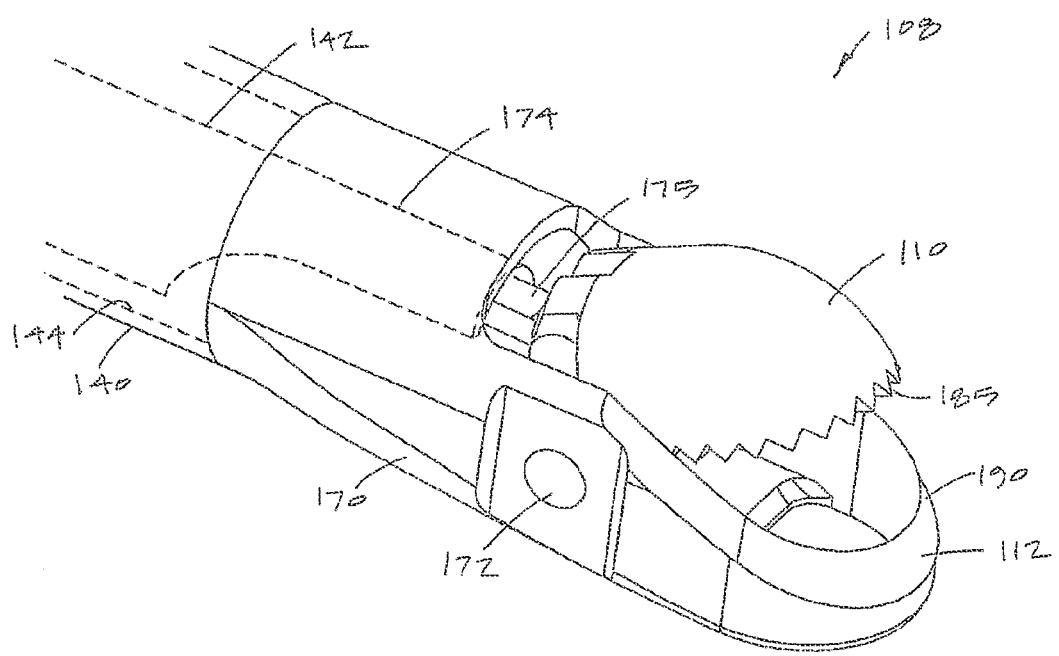
FIG. 3 is a detailed view of a working end of a probe constructed in accordance with the principles of the present invention.
Figure 4A:
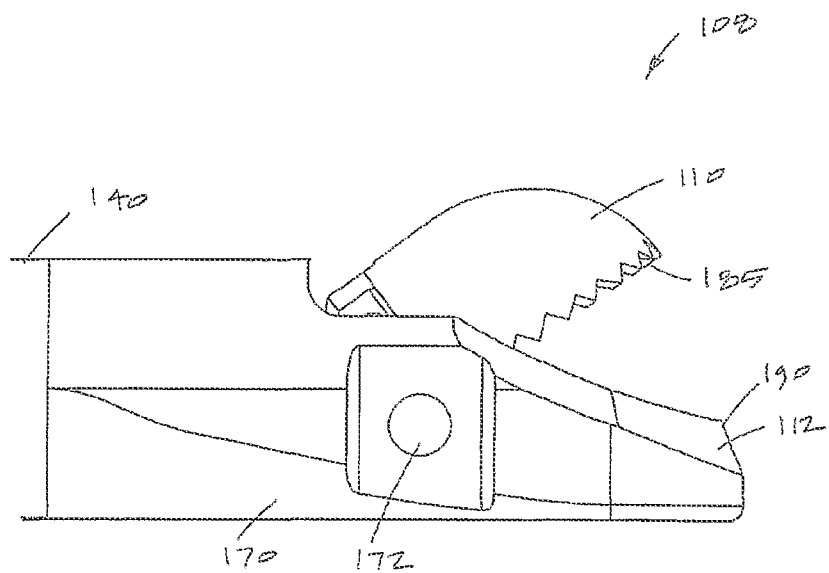
FIG. 4A is an enlarged side view of the working end of the probe of FIG. 1 in a jaw-open position.
Figure 4B:
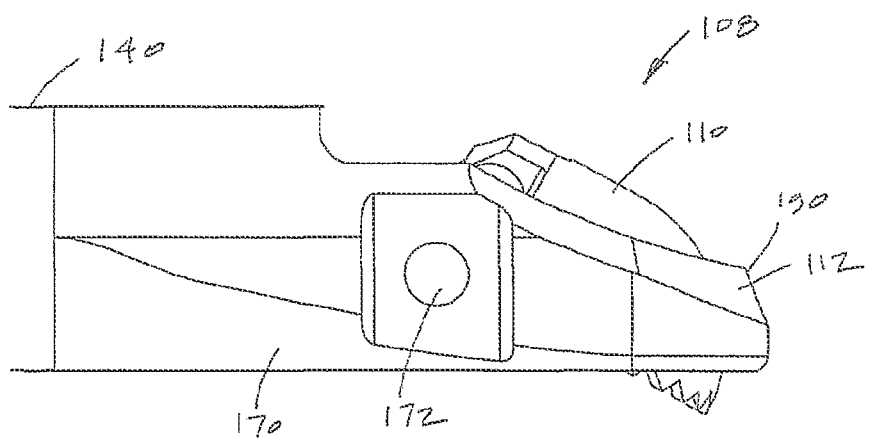
FIG. 4B is a side view of the working end of FIG. 4A in a jaw-closed position.
Figure 5A:
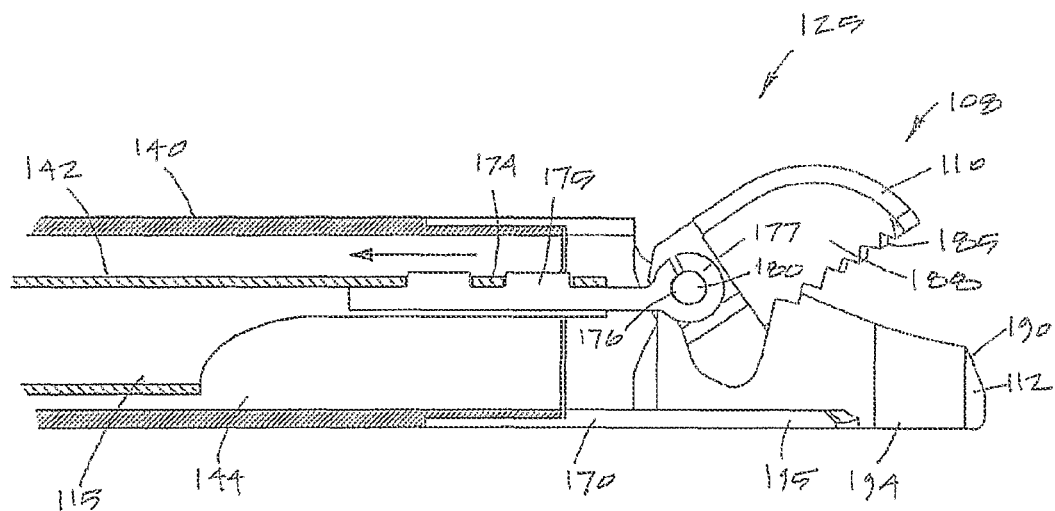
FIG. 5A is a longitudinal sectional view of the working end of FIG. 4A in the jaw-open position showing a portion of the jaw actuation mechanism.
Figure 5B:
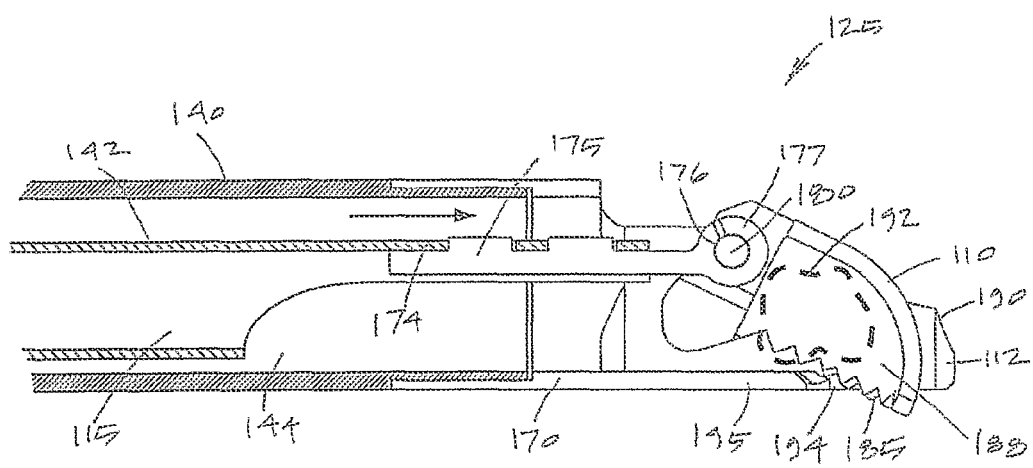
FIG. 5B is a sectional view of the working end of FIG. 4B in the jaw-closed position.

As can be seen in FIGS. 1, 3 and 4A-5B, the second or lower jaw 112 and lower jaw housing 170 is immobile and fixed to outer sleeve 140. The upper jaw 110 pivots around pivot point 172 in the lower jaw housing 170. The actuation member 142 can comprise a sleeve with passageway 115 therein and a distal end 174 coupled to an actuation rod 175 with a transverse bore 176 in a collar portion 177 that surrounds a transverse shaft 180 in the upper jaw 110. Thus, it can be seen how reciprocation of the actuating member 142 can move the first or upper jaw 110 relative to the second or fixed lower jaw 112. It should be appreciated that both the upper and lower jaw members of the jaw structure can be moveable as is known in biopsy punches and similar end effectors on medical cutting probes. In FIG. 3, the upper jaw 110 is fabricated of a high-strength metal, but it should be appreciated that such a jaw also can be fabricated out of a ceramic, such as the ceramics with a high fracture toughness as described in co-authored U.S. Pat. Nos. 9,585,675 and 9,603,656, which are incorporated herein by this reference. The lower jaw 112 likewise can be fabricated from a metal or a suitable ceramic with a sharp cutting edge.

Referring to FIGS. 3, 4A-4B and 5A-5B, it can be seen that upper jaw 110 is cup-shaped as is known in biopsy punches or meniscal punches for resecting tissue. The upper jaw 110 has a gripping and/or cutting edge 185 that extends in a U-shape around interior cavity 188 of the jaw. The lower jaw 112 has a cooperating U-shaped sharp cutting edge 190. It can be understood from FIGS. 4A-5B, the closing of jaw structure 108 shears tissue between cutting edges 185 and 190 to thus capture a tissue chip 192 (FIG. 5B) in the jaw's interior cavity 188. In the closed position of FIGS. 4B and 5B, it can be seen that the U-shaped edge 185 of the upper jaw 110 passes into U-shaped slot 194 in baseplate portion 195 of the lower jaw housing 170. Thereafter, the tissue chip 192 can be aspirated through interior passageway 115 by the negative pressure source 160 and be collected in a collection reservoir 196 (see FIG. 8).

Figure 6:
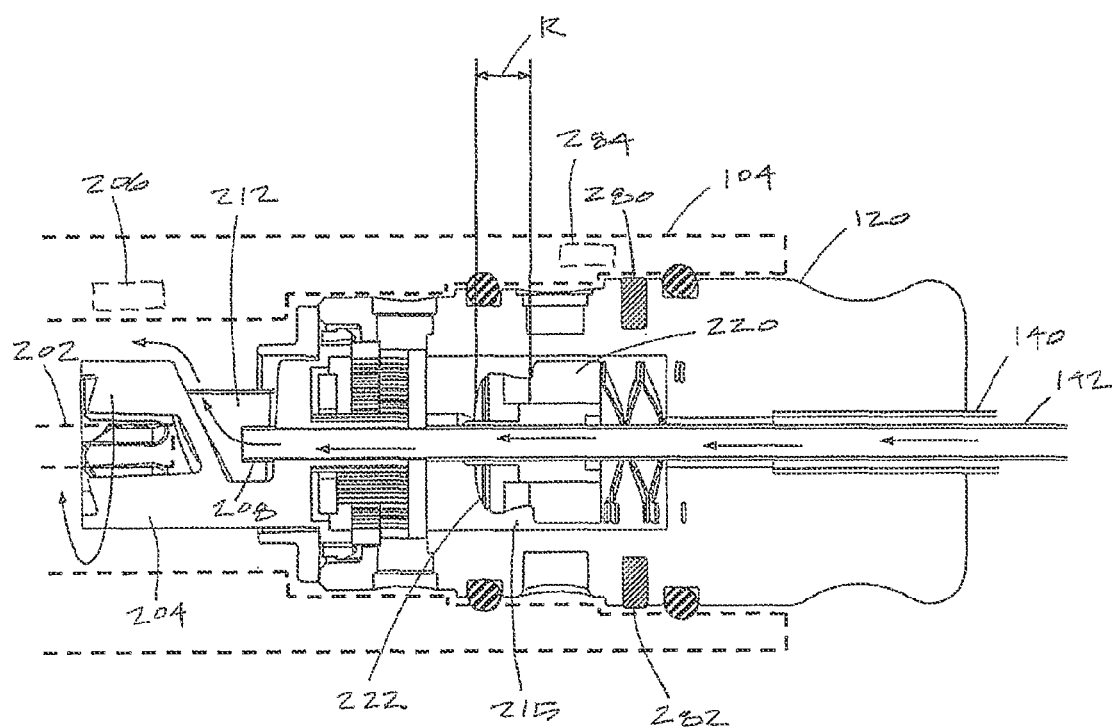
FIG. 6 is a longitudinal sectional view of the hub of the probe of FIG. 1 taken along line 6-6 of FIG. 1 showing a gear mechanism and a mechanism for converting rotational motion to linear motion to actuate the jaw structure at a selected CPS rate (cycles per second).
Figure 7A:
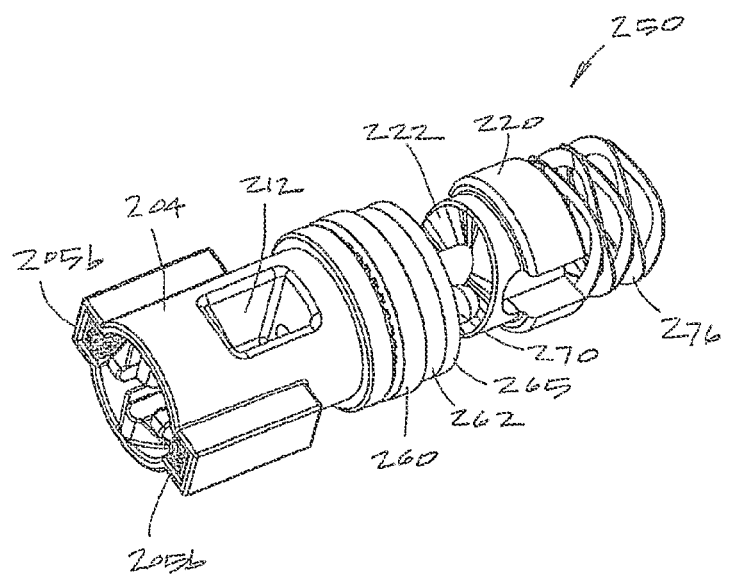
FIG. 7A is a perspective view of the planetary or epicyclic gear mechanism of the probe hub of FIG. and the rotation-to-linear motion mechanism.
Figure 7B:
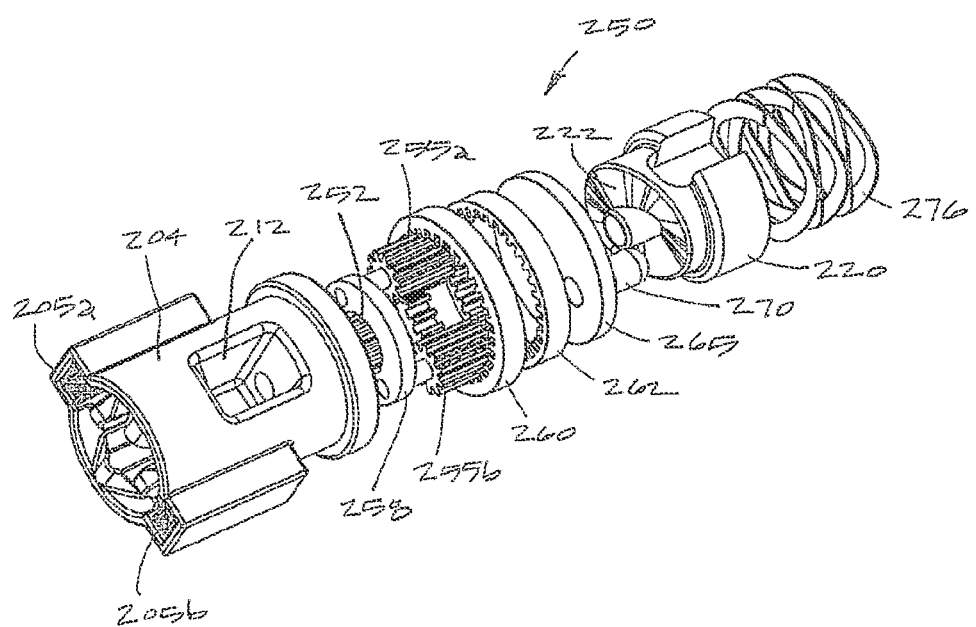
FIG. 7B is an exploded view of the components of the epicyclic gear mechanism of FIG. 7A.

Now turning to FIGS. 6 and 7A-7B, the mechanism that converts the rotation of the rotating shaft 202 of motor drive 105 to linear motion of actuation member 142 can be described. In one aspect of the invention, when cutting somewhat hard tissue such as meniscus, what is needed is an amplification of force that can be applied by the cutting edges of the jaw structure 108 against the targeted tissue. In FIGS. 6 and 7A, it can be seen rotatable drive coupling 204 is adapted for engaging the motor shaft 202 as is known in the art. The drive coupling 204 carries magnets 205a in 205b that cooperate with a Hall sensor 206 in the hand piece (FIGS. 2 and 6) to the acquire signals relating to the rotational orientation of drive coupling 204. The controller and processor 150 then can determine the open and closed positions of the jaw structure 108 depending on the rotational orientation of the coupling 204. It can be seen that the proximal end 208 of the actuator member 142 extends through the drive coupling 204 to the opening 212 in the side of drive coupling 204 to allow tissue chips (e.g., tissue chip 195 in FIG. 5B) to be extracted through the hub 120. The actuation member 242 is fixed in a collar 220 having a cam surface 222 the rotates in interior chamber 215 of the hub 120 (FIG. 6).

In one aspect of the invention, the drive coupling 204 engages the gear reduction mechanism comprising an epicyclic gear train assembly 250 which also may be called a planetary gear mechanism. FIG. 7A shows the epicyclic gear train assembly 250 removed from the hub 120 of FIG. 6. FIG. 7B depicts the gear train 250 of FIG. 7A in an exploded view showing the sun gear 252, the planet gears 255a and 255b, carrier ring 258, stationary output ring gear 260, output ring gear 262 and output ring gear transfer plate 265 as is known in the art. FIGS. 7A-7B also show a projecting element or stud 270 that interfaces with the angled cam surface 222 on rotating collar 220 that is adapted to convert rotational motion to linear motion. Thus, rotation of rotating motor shaft 202 rotates the sun gear 252 and planet gears 255a and 255b to provide gear reduction and ultimately rotate the output ring gear transfer plate 265 and rounded-end stud 270 to actuate the non-rotatable cam surface 222, which in turn reciprocates the actuator member 242. A spring 276 is provided to urge the rotating collar 220 carrying the cam surface 222 toward a proximal or retracted position in the interior chamber 215 of the hub 120. The stroke of reciprocation R is shown in FIG. 6 which is required to open and close the jaw structure 108.

In one aspect of the invention, the epicyclic gear mechanism of FIGS. 6-7B is configured for amplifying the output torque of the motor drive to increase closing forces of the jaw structure. In one variation, the gear mechanism increases the motor output torque by a factor of at least 10 or by a factor of at least 20. In some variations, the gear mechanism increases the motor output torque by at a factor of at least 40, and often by a factor of at least 60. In another aspect, the gear mechanism increases the motor output torque to at least 10 in-lbs, at least 40 in-lbs, at least 60 in-lbs, or at least 80 in-lbs.

In another aspect of the invention, the processor 150 is adapted to operate the motor drive 105 to move the jaw structure between open and closed positions at a rate of at least 1 CPS (cycles per second). Typically, the motor drive is configured to move the jaw structure between open and closed positions at a rate between 1 CPS and 100 CPS, and often at a rate between 1 CPS and 10 CPS. The processor also can be configured to control the motor drive 105 to stop movement of a first jaw relative to a second jaw in a selected default position, which typically is a closed position but also can be an open position. It can be understood that the jaw must be in a closed position for introduction into a patient's body, therefore a closed position is the typical default position. However, when the physician has positioned the working end 125 in a treatment site, the jaw structure 108 preferably would be in an open position. Therefore, a button (156a-156d) on the hand piece 104 can be adapted to move the jaws from the default closed position to the open position.

In use, an actuator button (156a-156d) can be used to close and open to jaw structure 108 in a single bite, or the actuator button can sequentially close and open the jaws at a selected rate. In one variation, an actuator button such as a joystick can increase the closing opening rate from a lower rate to a higher rate. Typically, an actuator button on the hand piece 104 actuates the motor drive 105 to move the jaw structure 108 between the jaw-open and jaw-closed positions at a rate of at least 1 CPS (cycles per second). More often, the rate of actuation is between 2 CPS and 10 CPS, although the rate could be higher, for example up to 100 CPS.

In another aspect of the invention, the processor 150 can be configured to modulate the negative pressure source 160 in response to actuation of the motor drive 105, so the negative pressure is actuated contemporaneously with closing and opening jaws. In another variation, the processor 150 can be configured to modulate the negative pressure source relative to a fully open jaw position, a partially open jaw position or a closed jaw position.

Figure 8:
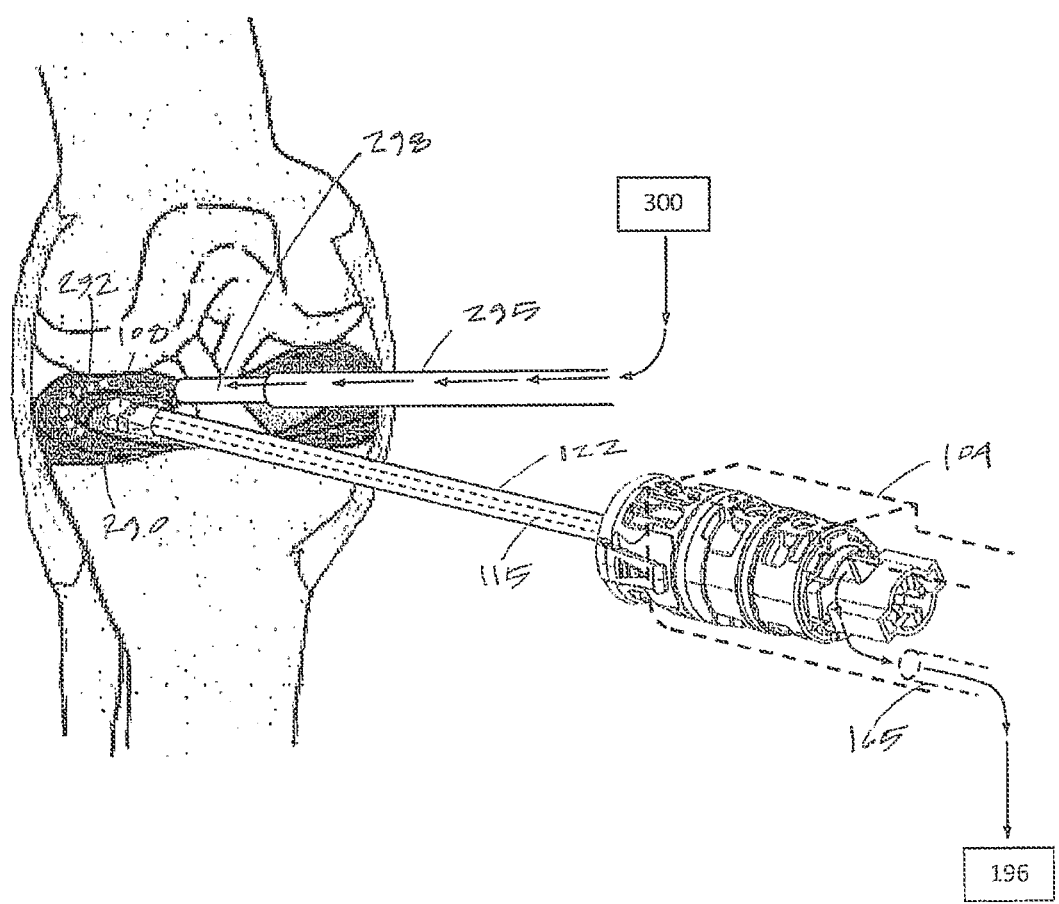
FIG. 8 is a schematic view of a method of using the probe of FIGS. 1-6 in a meniscectomy procedure.

Now referring to FIGS. 1, 2 and 8, a method of using probe 100 of FIG. 1 is shown schematically in a meniscectomy procedure. First, the physician inserts the probe 100 of FIG. 1 into the hand piece 104 of FIG. 2. Magnets 280 and 282 in the probe hub 120 (FIG. 6) are oriented relative to relative to a Hall sensor 284 in the hand piece (FIG. 2) such that the controller-processor 150 identifies the type of probe coupled to the hand piece 104 and the up or down orientation of the probe. The use of a Hall sensors and magnets in a probe hub for (i) device identification and (ii) positioning of working end components of arthroscopic tools is further described in co-pending U.S. patent application Ser. No. 15/454,432 filed Mar. 9, 2017 which is incorporated herein by this reference. Based on such a device identification, the controller then selects the appropriate processor algorithms for operating the probe 100. The hand piece 104 is adapted to receive and operate multiple different tools including rotating mechanical shavers, reciprocating electrosurgical shavers, hook shaped electrosurgical devices and articulating radiofrequency devices. Therefore, device identification is necessary because each different type of probe requires different processor algorithms to control the motor drive 105, the negative pressure source 160 and potentially the RF source 285, as will be described below.

Returning to FIG. 8, the cut-away view of the patient's knee shows the meniscus 290 with a "bucket handle" tear indicated at 292. The physician introduces a cannula 295 into the joint space and then advances an endoscope 298 through the cannula to view the treatment site. A fluid source 300 is coupled to the cannula 255 to introduce a distention fluid, such as saline, into the treatment site. Thereafter, the physician introduces the shaft 122 and working end of the probe 100 into the treatment site with the jaw structure 108 in the default closed position. Thereafter as shown in FIG. 8, the physician uses an actuator button (156a-156d) on the hand piece 104 (FIG. 2) to move the jaw structure 108 to the jaw-open position. Next, the physician manipulates working end to position the open jaw structure 108 over the meniscus tissue of the tear 292 targeted for resection. Thereafter, the physician uses an actuator button (156a-156d) to close the jaw structure with high closing forces in a single bite, or sequentially in repeated bites. The physician can then move the jaw structure 108 about the treatment site to remove targeted tissue. The resected tissue chips are then aspirated through the interior channel 115 of the probe 100 and flow channel 165 of hand piece 104 to be collected in collection reservoir 196.

Figure 9A:
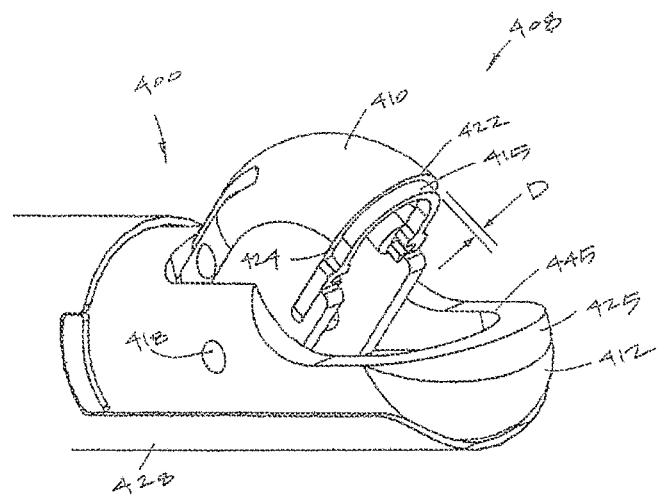
FIG. 9A is a perspective view of a working end of a probe with an electrosurgical jaw structure with the jaws in an open position.
Figure 9B:
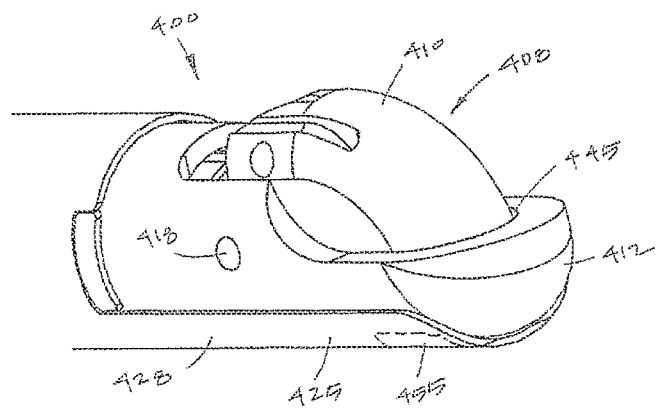
FIG. 9B is a view of the working end of the electrosurgical jaw structure of FIG. 9A with the jaws in a closed position.

FIGS. 9A-9B illustrate another working end 400 of a probe with a jaw structure 408 with first or upper jaw 410 and lower jaw 412. In this variation, the upper jaws 410 again has a cup shape and carries an active electrode 415 that extends in a U-shape around the perimeter of the upper jaw 410. The upper jaw 410 is formed of a dielectric material such as a ceramic with the electrode 415 secured thereto. The electrode is operatively coupled to an RF source 285 as shown in FIG. 2. The upper jaw 410 rotates around pivot pin 418 and can be actuated as the previous embodiment above. As can be seen in FIG. 9A, the electrode 415 can be set back from the outermost edge 422 of the jaw face 424 by a dimension D which can be from 0.05 mm to 2 mm, so that the lower jaw 412 can function as a return electrode 425. Alternatively, the lower jaw can comprise a ceramic material and the elongate outer sleeve 428 can function as a return electrode indicated at 425'. It can be understood from FIGS. 9A-9B that the cavity 440 in the jaws when closed allows the electrode 415 with a cutting current from RF source 285 to shear tissue chips from targeted tissue as the electrode 415 passes the edge 445 of the lower jaw 412. The targeted tissue is submerged in saline as in known in arthroscopic surgeries. The targeted tissue typically comprises at least one of cartilage, meniscus, connective tissue, tendons, and ligaments as in any arthroscopic procedure.

An electrosurgical probe as shown in FIGS. 9A-9B can connect RF current from RF source 285 through the hand piece 104 (FIG. 2) to the probe hub and jaw structure 408 as further described in co-pending U.S. patent application Ser. No. 15/454,390 filed Mar. 9, 2017 and Ser. No. 15/454,432 filed Mar. 9, 2017 which are incorporated herein by this reference.

In the variation of FIGS. 9A-9B, the upper jaw 410 rotates on a pivot pin 418, but it should be appreciated that flex hinges or living hinges are also possible. In another variation, it should be appreciated that another electrode 455 (see FIG. 9B) can be disposed on an outer surface of the lower jaw 412, or either jaw surface, which can be configured for ablation or coagulation as is known in the art.

Figure 10:
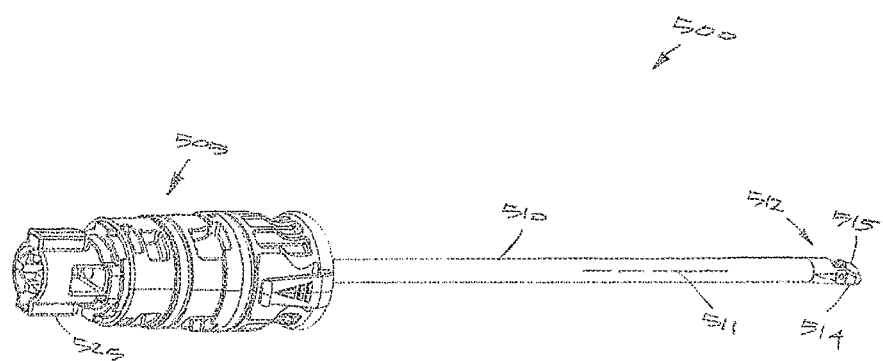
FIG. 10 is a perspective view of another variation of a probe for cutting meniscus.

FIG. 10 is a perspective view of an alternative variation of a meniscus cutting device 500 which again includes a proximal hub 505 coupled to an elongate shaft 510 that extends along a longitudinal axis 511 to the distal jaw structure 512. In this variation, the jaw structure 512 again includes a stationary lower jaw 514 and a moveable upper jaw 515 with a sharp cutting edge adapted for cutting meniscus.

The embodiment of FIG. 10 differs from previous embodiments in that it uses a screw-based conversion mechanism for converting rotational motion of the motor shaft to a linear motion rather than the rather than the planetary or epicyclic gear mechanisms described previously. The screw-based conversion mechanism comprises helically threaded drive components to convert rotational motion from the motor drive shaft in the hand piece to a pivotal reciprocating motion of the jaws or other end effector. In particular, the use of helically threaded driving components can significantly amplify the torque force applied by the motor drive shaft to increase the closure force applied to the jaws.

Figure 11A:
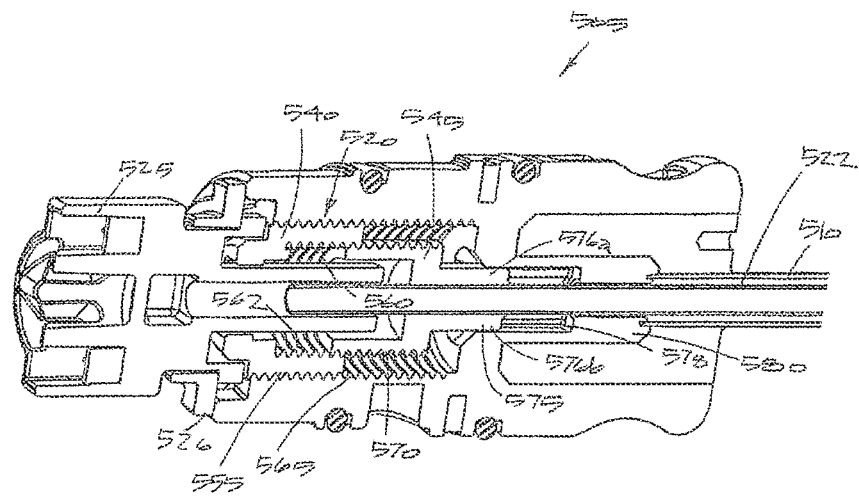
FIG. 11A is a sectional view of the hub of the probe of FIG. 10 showing a drive mechanism for converting rotational motion to linear motion using a differential screw assembly for increasing motor output torque to provide substantial jaw-closing forces, with the drive mechanism in a first position corresponding to a jaw-open position.
Figure 11B:
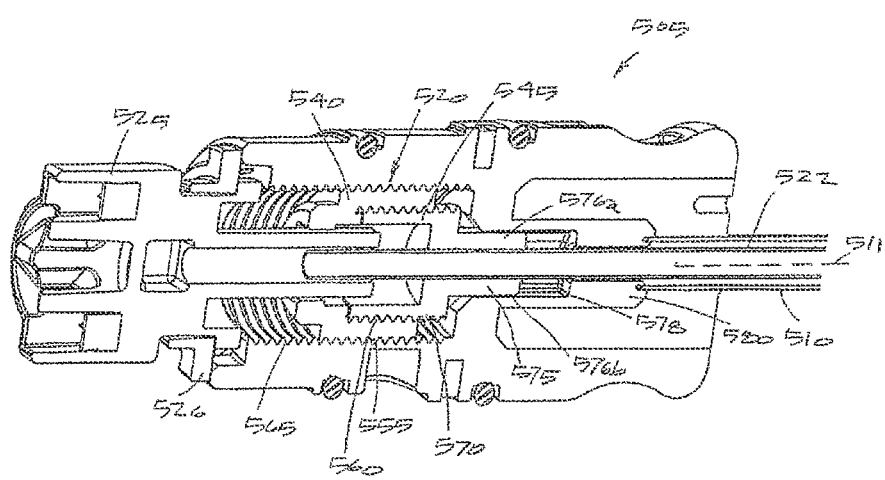
FIG. 11B is a sectional view of the hub of FIG. 11A showing the drive mechanism in a second position corresponding to a jaw-closed position.
Figure 12:
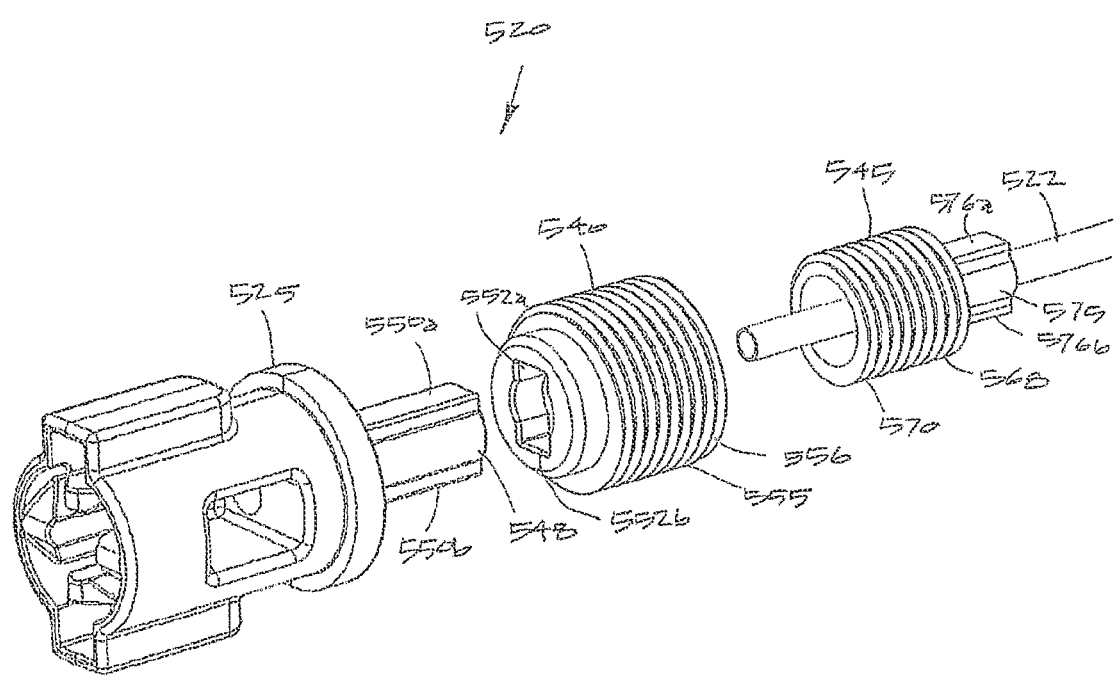
FIG. 12 is an exploded view of the components of the drive mechanism of FIGS. 11A-11B separated from the hub.

Referring now to the sectional views of FIGS. 11A-11B and the exploded view of FIG. 12, an exemplary screw-based conversion mechanism comprises a drive structure or assembly 520 including a plurality helically threaded components that are adapted to convert rotational motion from the drive shaft 202 of a motor drive 105, as illustrated in FIG. 2 above, into a longitudinal motion or "stroke" of the actuator member 522 which is reciprocatably mounted in the shaft 510. Because of the "gear reduction" provided by the threaded components, the high speed, low torque force from the motor shaft can be converted into a lower speed closure of the jaw structure 512 having sufficient force to cut dense meniscal tissue.

Referring to FIG. 11A, a drive coupling 525 configured to engage and be rotated by the drive shaft 202 in the hand piece 104 (FIG. 2) is mounted to rotates in a proximal end 526 of the hub 505. The drive coupling 525 includes a distal extension 548 which extends into a cylindrical cavity 567 formed in the proximal end of the hub and having a helically threaded wall. The drive coupling 525 rotates relative to the hub 505 but cannot move longitudinally.

The distal extension 548 of the drive coupling 525 rotates a transfer element 540 which transfers axial motion to an output element 545 that drives the jaw actuator member 522. The transfer and output elements 540 and 545 are threated cylinders which together with the helically threaded wall of cavity 567 provide a differential screw mechanism that provides a high level of mechanical advantage which increases an axial output force of the output element to thereby increase the closing forces applied to and by the jaw structure 512. FIG. 11A illustrates the drive structure 520 in a first position that corresponds to a jaw-open (actuator member 522 proximally retracted) configuration and FIG. 11B illustrates the drive structure 520 in a second position that corresponds to a jaw-closed (actuator member 522 distally advanced) configuration.

More specifically, referring to FIGS. 11A and 12, the distal extending portion 548 of the drive coupling 522 has an elongated tubular shape with first and second longitudinal key portions 550a and 550b that are received in slot portions 552a and 552b of a central passage in the transfer element 540. The key portions 550a and 550b are configured to applying a rotational force to the transfer element 540 as the drive coupling 525 rotates as well as to axially translate (slide in a longitudinal direction) in the slot portions 552a and 552b as the transfer element 540 axially translates due to the interaction of external helical threads 555 on the transfer element with the helically threaded wall of the cylindrical cavity 567 as the drive coupling 525 rotates. The drive coupling 525 is mounted in a bearing 525a that prevents it from moving axially, i.e. the drive coupling remains axially fixed while it rotates.

The transfer element 540 has a cylindrical shape with outer helical threads 555 around its exterior surface 556 and inner helical threads 560 (FIGS. 11A and 11B) around a central bore 562 which extends along a longitudinal axis 511 of the drive element 540. Thus, the outer and inner helical threads 555 and 560 are concentric with one another about the axis 511 over a length of the transfer element 540.

As further can be seen in FIG. 11A, the outer helical threads 555 around the exterior surface 556 of the transfer element 540 engage the cooperating helical threads 565 formed over the interior wall of the cylindrical cavity 567 of the hub 505 so that the transfer element 540 will move longitudinally within cylindrical cavity 567 as the first drive element 540 is rotated by the drive coupling 525. It can be understood from FIGS. 11A and 12 that the key portions 550a and 550b of the extending portion 548 of the drive coupling 520 slidably engage the receiving slots 552a and 552b in the first drive element 540 to thus rotate the drive element 540 which advances or retracts in the hub 505 depending on the direction in which the drive coupling 525 is rotated by an associated motor drive, such as motor drive unit 105.

As also can be seen in FIGS. 11A and 12, the output element 545 has an outer surface 568 configured with helical threads 570 that engage the cooperating inner helical threads 560 in the bore 562 of the transfer element 540. Thus, it can be understood that rotation of the transfer element 540 will drive the output element 545 longitudinally relative to the hub 505. The transfer element 545 also has a distally extending distal portion 575 that has key portions 576a and 576b that slide in slots 578a and 578b in a distal portion 580 of the hub 505 so that the output element 545 is able to move longitudinally but not rotationally. The actuator member 522, which can be a stainless steel hypo tube, is fixed in the transfer element 545, e.g. by adhesives, pins, press fit or other suitable means.

In this way, rotation of the drive coupling 520 causes rotational and longitudinal movement of the transfer element 540. The transfer element 540 threadably engages the helical threads 565 formed over the interior wall of the cylindrical cavity 567, causing the transfer element to axially advance or retract. Concurrently, the inner threads transfer element 540 threadably engages the second drive element 545 to thereby cause the second drive element 545 to move longitudinally but not helically to thus actuate the jaw structure.

As can be understood from the description of previous embodiments, a controller and software algorithm is configured to control operation of the motor to rotate the drive coupling 525 a predetermined number of rotations, which then moves the first and second drive elements 540, 545 in a predetermined manner, to move the jaw structure 512 from a jaw-open position to a jaw-closed position. The controller algorithm is further adapted to reverse rotation of the motor to move the jaw structure 512 from the jaw-closed position to the jaw-open position. Further, the controller algorithm is adapted to operate the motor to close and open to jaw structure sequentially at a rapid rate, for example, from one cycle per second to 20 cycles per second.

In one particular variation, the jaw structure 512 can be actuated from the jaw-open to the jaw-closed position with the actuator member 522 moving approximately 1.65 mm. The first drive element 540 has 1.25 mm helical (first) threads 550 on its exterior surface which engages the hub threads. The second helical threads 555 in the bore of the first drive element 540 are 1.0 mm threads that engage the second drive element 545. In this variation, 6.6 revolutions of the drive coupling 525 will then translate the actuator member 522 in a stroke of 1.65 mm to move the jaw structure from the jaw-open position to the jaw-closed position, or 0.25 mm for every rotation of the drive coupling 520. In this example, the total longitudinal displacement of the first drive element 540 is 8.25 mm.

The drive structure 520 described above uses multiple drive components to increase torque, but it should be appreciated that a single screw mechanism could also be used to convert rotational motion to linear motion, and falls within the scope of the invention. The use of a single helically rotating component, rather than the differential screws of the variation of FIGS. 11A-12 could require the very five thread pitch which could be disadvantageous as such thread design could be less robust.

In the variation shown in FIGS. 11A-12, the helical drive structure amplifies the output torque of the motor drive by at least a factor of 10 to increase the closing force of the jaw structure. In similar variations, the drive structure described above can increase the motor output the factor of at least 20 or at least 60. Stated another way, the drive structure can increase the motor output torque to at least 10 in-lbs, 40 in-lbs, 60 in-lbs, or 80 in-lbs.

In another variation, a probe with a jaw opening and closing mechanism similar to that described above can operate a working end comprising a mechanical scissors or shears for cutting tissue.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An arthroscopic device for use with a hand piece that includes a motor drive with a rotatable shaft, said arthroscopic device comprising;
   an elongate probe extending along a longitudinal axis;
   a proximal hub on a proximal end of the elongate probe, wherein the proximal hub is configured for detachable coupling to the hand piece;
   an openable-closeable jaw structure on a distal end of the elongate probe; and
   a conversion mechanism carried by the hub for converting a rotational motion of the rotatable shaft to a longitudinal motion of an actuator member, wherein the actuator member is configured for driving the openable-closeable jaw structure between a jaw-open position and a jaw-closed position,
   wherein the conversion mechanism comprises a first drive element and a second drive element, the first drive element including external helical threads that engage internal helical threads in the hub, the second drive element including external helical threads that engage internal helical threads in the first drive element.

2. The arthroscopic device of claim 1, wherein the internal helical threads and the external helical threads of the first drive element have different thread pitches.

3. An arthroscopic device for use with a hand piece that includes a motor drive with a rotatable shaft, said arthroscopic device comprising:
   an elongate probe extending along a longitudinal axis;
   a proximal hub on a proximal end of the elongate probe, wherein the proximal hub is configured for detachable coupling to the hand piece;
   an openable-closeable jaw structure on a distal end of the elongate probe; and
   a conversion mechanism carried by the hub for converting a rotational motion of the rotatable shaft to a longitudinal motion of an actuator member, wherein the actuator member is configured for driving the openable-closeable jaw structure between a jaw-open position and a jaw-closed position,
   wherein the conversion mechanism comprises at least a first drive element including external helical threads that engage internal helical threads in the hub wherein rotation of the first drive element axially translates the first drive element relative to the hub,
   wherein the conversion mechanism further comprises at least a second drive element including external helical threads that engage internal helical threads in the first drive element, wherein rotation of the first drive element to axially translate the first drive element relative to the hub axially translates the second drive element in a direction opposite to that of the first drive element.

4. The arthroscopic device of claim 3, wherein the second drive element is nested within a central cavity in the first drive element so that the external threads on the second drive element concentrically engage the inner helical threads in the first drive element which are disposed on an inner wall of the central cavity of the first drive element.

5. The arthroscopic device of claim 4 further comprising a rotatable drive coupling configured to: (i) be engaged and driven by the rotatable shaft of the motor drive; and (ii) couple to and rotate the first drive element.

6. The arthroscopic device of claim 5, wherein the rotatable drive coupling is inhibited from axial translation, the first drive element is free to rotate and axially translate, and the second drive element is inhibited from rotation and free to axially translate.

7. The arthroscopic device of claim 6, wherein the actuator member is coupled to a pivot mechanism for opening and closing the openable-closeable jaw structure.

8. The arthroscopic device of claim 7, wherein respective longitudinal portions of the internal helical threads and the external helical threads of the first drive element overlap one another.

9. The arthroscopic device of claim 8, wherein the internal helical threads and the external helical threads of the first drive element have different thread pitches.

10. The arthroscopic device of claim 9, wherein the different thread pitches are configured to amplify torque in moving the openable-closeable jaw structure from the jaw-open position toward the jaw-closed position.

11. The arthroscopic device of claim 10, wherein the conversion mechanism is configured to move the actuator member longitudinally in a stroke ranging from 0.5 mm to 5 mm to actuate the openable-closeable jaw structure from the jaw-open position to the jaw-closed position.

12. The arthroscopic device of claim 11, wherein the conversion mechanism is configured to convert from 1 to 20 rotations of the rotatable drive coupling to provide said stroke.

13. The arthroscopic device of claim 12, wherein the conversion mechanism is configured to convert from 2 to 10 rotations of the rotatable drive coupling to provide said stroke.

14. The arthroscopic device of claim 3 in combination with a controller for controlling the rotatable shaft of the motor drive, wherein the controller can actuate the rotatable shaft to: (i) rotate the rotatable shaft in a first rotational direction to move the openable-closeable jaw structure toward the jaw-closed position; and rotate the rotatable shaft in a second rotational direction to move the openable-closeable jaw structure toward the jaw-open position.

15. The arthroscopic device of claim 14, wherein the controller is configured move the openable-closeable jaw structure from the jaw-open position to the jaw-closed. position and back to the jaw-open position at a rate ranging from once per second to 20 times per second.

16. The arthroscopic device of claim 14, wherein the controller is configured move the openable-closeable jaw structure to a default jaw-open position upon de-activation of use by an operator.

17. The arthroscopic device of claim 14, wherein the controller is configured move the openable-closeable jaw structure to a default jaw-closed position upon de-activation of use by an operator.

18. The arthroscopic device of claim 14, wherein the controller is configured to allow actuation of the openable-closeable jaw structure to close and open a single time.

19. An arthroscopic system, comprising:
a hand piece including a motor drive with a rotatable shaft;
an elongate probe extending along a longitudinal axis from a proximal hub to a distal openable-closeable jaw structure, wherein the proximal hub is configured for detachable coupling to the hand piece;
a rotatable drive coupling carried by the proximal hub for engaging the rotatable shaft of the motor drive;
a conversion mechanism in the proximal hub for converting rotational motion of the rotatable drive coupling to longitudinal motion of an actuator member adapted for actuating the openable-closeable jaw structure between a jaw-open position and a jaw-closed position, wherein the conversion mechanism comprises a first drive element and a second drive element, the first drive element including external helical threads that engage internal helical threads in the hub, the second drive element including external helical threads that engage internal helical threads in the first drive element; and
a controller configured to operate the motor drive to move the operable-closeable jaw structure from the jaw-open position to the jaw-closed position and back to the jaw-open position at a rate ranging from once per second to 20 times per second.

20. The arthroscopic system of claim 19, wherein the rotatable drive coupling is inhibited from axial translation in the proximal hub, and the first drive element is free to rotate and axially translate in the proximal hub.

21. The arthroscopic system of claim 19, wherein the first drive element is rotatable in the proximal hub to axially translate the first drive element in the proximal hub in a first direction while the second drive element is axially translating in the proximal hub in a second direction that is opposite the first direction.

22. The arthroscopic system of claim 21, wherein the second drive element is nested within a central cavity in the first drive element so that the external threads on the second drive element concentrically engage the inner helical threads in the first drive element which are disposed on an inner wall of the central cavity of the first drive element.

23. The arthroscopic system of claim 21, wherein respective longitudinal portions of the internal helical threads and the external helical threads of the first drive element overlap one another.

24. The arthroscopic system of claim 21, wherein the internal helical threads and the external helical threads of the first drive element have different thread pitches.

25. The arthroscopic system of claim 24, wherein the different thread pitches are configured to amplify torque in moving the operable-closeable jaw structure from the jaw-open position toward the jaw-closed position.

26. The arthroscopic system of claim 19, wherein the conversion mechanism is configured to move the actuator member longitudinally in a. stroke ranging from 0.5 mm to 5 mm to actuate the openable-closeable jaw structure from the jaw-open position to the jaw-closed position.

27. The arthroscopic system of claim 19, wherein the conversion mechanism is configured to convert from 1 to 20 rotations of the rotatable drive coupling to provide said stroke.

28. The arthroscopic system of claim 19, wherein the conversion mechanism is configured to convert from 2 to 10 rotations of the rotatable drive coupling to provide said stroke.

\* \* \* \* \*